United States Patent [19]

Kezuka et al.

[11] Patent Number: 5,336,803
[45] Date of Patent: Aug. 9, 1994

[54] PROCESS FOR PRODUCING AN ORGANIC CARBONATE

[75] Inventors: Hiroaki Kezuka, Tochigi; Fumio Okuda, Sodegaura, both of Japan

[73] Assignee: Idemitsu Kosan Co., Ltd., Tokyo, Japan

[21] Appl. No.: 848,117

[22] Filed: Mar. 9, 1992

[30] Foreign Application Priority Data

Mar. 14, 1991 [JP] Japan .................. 3-073621
Jan. 16, 1992 [JP] Japan .................. 4-005613

[51] Int. Cl.$^5$ ............................... C07C 69/96
[52] U.S. Cl. ........................... 558/277; 558/274
[58] Field of Search ......................... 558/277, 274

[56] References Cited

U.S. PATENT DOCUMENTS

| | | | |
|---|---|---|---|
| 1,638,014 | 8/1927 | Mitchell | 558/277 |
| 3,114,762 | 12/1963 | Mador et al. | 260/463 |
| 3,579,568 | 5/1971 | Heck et al. | 558/277 |
| 4,201,721 | 5/1980 | Hallgren | 260/463 |
| 4,281,174 | 7/1981 | Current | 560/204 |
| 4,335,051 | 6/1982 | Buysch et al. | 558/277 |
| 4,349,485 | 9/1982 | Hallgren | 260/463 |
| 4,434,105 | 2/1984 | Buysch et al. | 558/277 |
| 4,582,645 | 4/1986 | Spencer | 558/277 |
| 4,652,667 | 3/1987 | Green | 558/277 |
| 4,898,946 | 2/1990 | Costanzi et al. | 558/277 |

FOREIGN PATENT DOCUMENTS

| | | |
|---|---|---|
| 0350697 | 1/1990 | European Pat. Off. |
| 0350700 | 1/1990 | European Pat. Off. |
| 45-11129 | 4/1970 | Japan. |
| 53-68747 | 6/1978 | Japan. |
| 54-135743 | 10/1979 | Japan. |
| 55-102539 | 5/1980 | Japan. |
| 55-94338 | 7/1980 | Japan. |
| 56-38143 | 9/1981 | Japan. |
| 56-38144 | 9/1981 | Japan. |
| 56-38145 | 9/1981 | Japan. |
| 62-126152 | 6/1987 | Japan. |
| 62-212305 | 9/1987 | Japan. |
| 1-165551 | 6/1989 | Japan. |
| 2-104564 | 4/1990 | Japan. |
| 2-142754 | 5/1990 | Japan. |

*Primary Examiner*—C. Warren Ivy
*Assistant Examiner*—Raymond Covington
*Attorney, Agent, or Firm*—Frishauf, Holtz, Goodman & Woodward

[57] ABSTRACT

A process for producing an organic carbonate which comprises reacting an organic hydroxy compound, carbon monoxide and oxygen in the presence of a catalyst comprising (a) palladium or a palladium compound, (b) a cuprous or cupric compound such as cupric acetate, (c) a quinone or an aromatic diol formed by reduction of the quinone or a mixture thereof such as hydroquinone, and (d) a halogenated onium compound such as $(C_4H_9)NBr$ is disclosed.

According to the invention, an organic carbonate such as diphenyl carbonate can be produced efficiently and economically.

19 Claims, No Drawings

PROCESS FOR PRODUCING AN ORGANIC CARBONATE

BACKGROUND OF THE INVENTION

1. Field of the Invention

The present invention relates to a process for producing an organic carbonate. More particularly, the present invention is concerned with a process for producing an organic carbonate efficiently from an organic hydroxy compound in the presence of a specified catalyst.

2. Description of the Related Arts

Heretofore, in order to produce organic carbonates, various processes have been proposed. For example, as the process for producing aromatic organic carbonates, a process using alkali metals and alkaline earth metals, basic quaternary ammonium, quaternary phosphonium or tertiary sulfonium compounds, hydroxides of alkali metals or alkaline earth metals, salts of strong bases and weak organic acids, bases such as primary amines, secondary amines, tertiary amines, primary amines salts or palladium (Japanese Patent Publication No. 38143/1981) as the catalyst; a process using a catalyst comprising Pd, and the base as mentioned above, an oxidizing agent (compounds of group IIIA, IVA, VA, VIA, IB, IIB, VIB, VIIB metals)(Japanese Patent Publication No. 38144/1981), a process using a catalyst comprising Pd and a base, oxidizing agent (Co, Mn) and a drying agent (Japanese Patent Publication No. 38145/1981); a process using a base and a VIII group metal in an oxidized state of +1 (Ru, Rh, Pd, Os, Ir, Pt) as a catalyst (Japanese Patent Application Laid-Open No. 68747/1978); a process using a base and VIII metal as the catalyst in an anhydrous condition (Specification of U.S. Pat. No. 4,201,721); a process using a catalyst comprising a base and VIII metal, and an oxidizing agent having a higher oxidization potential than VIII metal (Japanese Patent Application Laid-Open No. 135743/1979); a process using a catalyst comprising Pd and a base, oxidizing agent, phase-transfer agent and a drying agent (Japanese Patent Application Laid-Open No. 102539/1980); a process using a catalyst comprising a base and a VIII group metal, and an oxidizing agent (Specification of U.S. Pat. No. 4,349,485); a process using a catalyst comprising Pd, Mn, $R_4N^+X^-$ (R indicates an alkyl group and X indicates a halogen) and quinone (Japanese Patent Application Laid-Open 104564/1990); a process using a catalyst comprising Pd, Co, $R_4N^+X^-$ (R and X are as defined above) and quinone (Japanese Patent Application Laid-Open No. 142754/1990); a process using a catalyst comprising Pd, an alkali metal or an alkaline earth metal or an onium iodide compound and zeolites (Japanese Patent Application Laid-Open No. 165551/1990) are mentioned. However, the above-mentioned processes for producing aromatic organic carbonates have a problem in that the yield was insufficient.

As the process for producing aliphatic organic carbonates, a process using Pd, Cu or Fe as the catalyst (U.S. Pat. No. 3,114,762); a process for producing divalent Cu ion (Japanese Patent Publication No. 11129/1970) are mentioned. These processes, however, have problems in that the rate of the catalytic reaction is low, and that a large amount of the catalyst is required. Further, according to these processes, the yield is insufficient.

On the other hand, as the carbonylation method using Pd component and quinone component, a process for producing oxalic diester using Pd $(NO_3)_2$ and quinones as the catalyst (Japanese Patent Application Laid-Open No. 94338/1980); a process for producing oxalic diester using Pd, quinone and a redox agent (U.S. Pat. No. 4,281,174), a process for producing cinnamic acid ester using Pd, quinone and a redox agent (Japanese Patent Application Laid-Open No.126152/1987); a process for producing dialkyl carbonate using Pt group, Cu and quinone (Japanese Patent Application Laid-Open No. 212305/1987) are mentioned. However, these carbonylation methods have many problems in that the kinds of the products to be produced are limited and that the yield of the desired product is not sufficient.

SUMMARY OF THE INVENTION

The present inventors have intensively studied to overcome the above problems in the prior art and to establish a process for producing efficiently an organic carbonate from an organic hydroxy compound.

As the result, it was found that the above object can be attained by using a catalyst comprising (a) palladium or a palladium compound, (b) a cuprous compound or a cupric compound, (c) a quinone, an aromatic diol formed by reduction of the quinone, or a mixture thereof, and (d) a halogenated onium compound. The present invention was accomplished based on such findings.

An object of the present invention is to provide an improved process for producing an organic carbonate which can be used as the starting material for various chemical products.

Another object of the present invention is to provide a process for producing various kinds of organic carbonates.

Still another object of the present invention is to provide a process for efficiently producing an organic carbonate with a small amount of catalyst.

The present invention provides a process for producing an organic carbonate which comprises reacting an organic hydroxy compound, carbon monoxide and oxygen in the presence of a catalyst comprising (a) palladium or a palladium compound, (b) a cuprous compound or a cupric compound, (c) a quinone, an aromatic diol formed by reduction of a quinone, or a mixture thereof, and (d) a halogenated onium compound.

DESCRIPTION OF PREFERRED EMBODIMENTS

The organic hydroxy compounds to be used in the process of the present invention vary depending on the kinds of the organic carbonate to be produced. For example, aliphatic monohydroxy or aliphatic polyhydroxy compounds having 1 to 6 carbon atoms, cycloaliphatic monohydroxy or cycloaliphatic polyhydroxy compounds having 3 to 15 carbon atoms, and aromatic monohydroxy or aromatic polyhydroxy compounds having 6 to 15 carbon atoms are mentioned. Aliphatic monohydroxy compounds include alcohols such as methanol, ethanol, propanol, butanol, pentanol, and hexanol; aliphatic polyhydroxy compounds include glycols (dihydroxy compounds) such as ethyleneglycol, propylene glycol, 1,4-butanediol, 1,5-pentanediol, and 1,6-hexanediol and trihydroxy compounds such as glycerol. Cycloaliphatic monohydroxy compounds include cyclic alcohols such as cyclopentanol, cyclohexanol and cycloheptanol; cycloaliphatic polyhydroxy compounds include alicyclic diols such as cyclopentandiols, and cyclohexanediols.

Aromatic monohydroxy compounds include phenolic compounds such as phenol, cresols, naphthols, p-methylphenols, and t-butylphenol (e.g. p-t-butylphenol); and aromatic polyhydroxy compounds include aromatic dihydroxy compounds such as phenolic compounds, for example catechol, hydroquinone, resorcinol, and 2,2-bis(4'-hydroxyphenyl)-propane (bisphenol A). If these phenolic compounds have an alkyl group as a substituent, the alkyl group having 1 to 6 carbon atoms, preferably 1 to 4 carbon atoms is preferred. Among the above-mentioned compounds, aromatic monohydroxy compounds or aromatic polyhydroxy compounds are suitably used.

Carbon monoxide to be reacted with the above-mentioned organic hydroxy compounds may be diluted with inert gas, or mixed with hydrogen. As the oxygen to be reacted with the above-mentioned organic hydroxy compounds, pure oxygen may be used, but usually oxygen diluted with inert gas, for example, oxygen-containing gas such as air can be used.

The catalyst to be used in the process of the present invention comprises components (a), (b), (c), and (d), as described above. Herein, with regard to the palladium compounds as component (a), for example, palladium chloride ($PdCl_2$), palladium bromide ($PdBr_2$), palladium iodide ($PdI_2$), palladium acetate ($Pd(OAc)_2$; Ac indicates an acetyl group), palladium nitrate ($Pd(NO_3)_2$), and palladium sulfate ($PdSO_4$) are mentioned. As palladium catalysts of deposited type, Pd/active carbon, Pd/alumina, Pd/silica, Pd/silica.alumina, Pd/zeolite and the like are mentioned. Cuprous or cupric compounds as component (b) include copper(I) chloride (cuprous chloride), copper(I) bromide (cuprous bromide), copper(I) iodide (cuprous iodide), copper(II) chloride(cupric chloride), copper(II) bromide (cupric bromide), copper(II) iodide (cupric iodide), copper(II) acetate, (cupric acetate), and copper(II) nitrate (cupric nitrate).

A quinone, an aromatic diol formed by reduction of the quinone, or mixtures thereof as component (c) includes various ones. For example, a quinone includes benzoquinone, 1,2-benzoquinone, 1,4-naphthoquinone, anthraquinone, and 1,4-phenanthrenequinone. Aromatic diols include ones formed by reduction of benzoquinone, 1,2-benzoquinone, 1,4-naphthoquinone, anthraquinone or 1,4-phenanthorenequinone, such as hydroquinone, catechol, 1,4-dihydroxynaphthalene, 9,10-dihydroxyanthracene, and 1,4-dihydroxyphenanthrene.

With regard to halogenated onium compounds as component (d), tetraalkylammonium halide (specifically, $Pr_4NCl$, $Bu_4NCl$, $Pr_4NBr$, $Bu_4NBr$, $Pr_4NI$ and $Bu_4NI$), tetraalkylphosphonium halide (specifically, $Pr_4PCl$, $Bu_4PCl$, $Pr_4PBr$, $Bu_4PBr$, $Pr_4PI$ and $Bu_4PI$), trialkylsulfonium halide (specifically, $Pr_3SCl$, $Bu_3SCl$, $Pr_3SBr$, $Bu_3SBr$, $Pr_3SI$ and $Bu_3SI$) are mentioned. Herein, Pr indicates a propyl group, and Bu indicates a butyl group.

The amount of the catalyst to be used in the process of the present invention is not limited particularly, but it is usually determined in the range of catalytic amounts. However, component (a) should be $10^{-5}$ to 1 mol, preferably $10^{-4}$ to $10^{-2}$ mol as Pd based on 1 mol of organic hydroxy compound for the starting material. If it is less than $10^{-5}$ mol, the reaction rate becomes impractically low. If it exceeds 1 mol, no effect corresponding to the amount is not obtained, which is economically disadvantageous. Component (b) is usually 1 to 100 mol, preferably 1 to 50 mol, based on 1 mol of Pd as component (a). Similarly, component (c) is usually 1 to 100 mol, preferably 1 to 50 mol, based on 1 mol of Pd as component (a), and component (d) is usually 1 to 100 mol, preferably 1 to 50 mol, based on 1 mol of Pd as component (a).

The process of the present invention proceeds also in the absence of solvent, but preferably it proceeds in the presence of solvent. As the solvents to be used there, for example, aliphatic hydrocarbons, cycloaliphatic hydrocarbons, aromatic hydrocarbons, halogenated hydrocarbons, ethers and esters are mentioned. Specific examples of the aliphatic hydrocarbons, cycloaliphatic hydrocarbons and aromatic hydrocarbons are hexane, heptane, cyclohexane, benzene, toluene, xylenes and the like; and specific examples of halogenated hydrocarbons are methylene chloride, chloroform, chlorobenzene and the like; and specific examples of ethers are dioxanes, anisole, diphenylether and the like; and specific examples of esters are methyl acetate, ethyl acetate, phenyl acetate, methyl propionate, ethyl pinonate and the like.

The reaction temperature is not limited particularly, but is usually 50° to 200° C., and preferably 70° to 150° C. At too high temperature, side reactions such as decomposition reaction undesirably occur, while at low temperature, reaction rate becomes impractically low. The reaction should usually be performed under pressure, since gaseous material including carbon monoxide and oxygen is used. Usually, the reaction pressure will be sufficient if the partial pressure of carbon monoxide is at least about 30 $kg/cm^2$, and the partial pressure of oxygen is at least 1 $kg/cm^2$. Taking the explosion limit into account, the partial pressure of oxygen is preferably about 5% by volume of the partial pressure of carbon monoxide. If the partial pressure of oxygen is too low, the reaction rate will be lowered, while if it is too high, a large-sized apparatus is required for reaction, and its construction will cost disadvantageously high.

The reaction system may be any of batch system, semi-continuous and continuous system. Herein, the state in the reaction system is a liquid phase or same mixed state of a liquid phase and a vapor phase. The state of the catalyst in the reaction system may be homogeneous or heterogeneous, and solvents and catalysts may be selected appropriately. Above-mentioned components of the material and catalyst can be diluted if necessary, and as the diluents for them,inert solvents such as saturated hydrocarbons are used in the liquid phase, and inert gases such as nitrogen, ethane, and propane are used in the vapor phase.

In the process of the present invention, organic hydroxy compound described above, carbon monoxide and oxygen are reacted in the presence of the above catalyst to produce an organic carbonate. The objective organic carbonate to be obtained in the reaction (that is, carbonate of organic hydroxy compound) include various ones. For example, when an organic hydroxy compound represented by the general formula: R—OH (R is an alkyl group having 1 to 6 carbon atoms including methyl, ethyl, propyl, butyl, pentyl, and hexyl group, or an aryl group having 6 to 15 carbon atoms including phenyl, methylnaphthyl, naphtyl, and butylphenyl group) is used, an organic carbonate represented by the general formula:

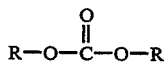

(R is as defined above) can be obtained. Specific examples of said organic compounds are dimethyl carbonate, diethyl carbonate, and diphenyl carbonate.

When an organic hydroxy compound represented by the general formula HO—$R^1$—OH ($R^1$ is an alkylene having 1 to 6 carbon atoms including ethylene, propylene, butylene, pentylene, and hexylene); or a divalent group which results by removing 2 hydroxy groups from the above-mentioned aromatic dihydroxy compounds, including phenylene, methylphenylene, and

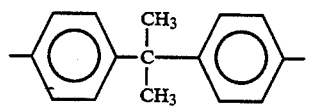

is used, an organic carbonate represented by the general formula:

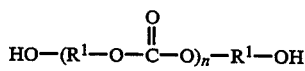

(R is as defined above, and n is an integer of at least 1) can be obtained.

The by-products obtained in that reaction include oxalate and salicylate of organic hydroxy compounds. Specific examples of these by-products are dimethyl oxalate, diethyl oxalate and phenyl salicylate. The objective product and the by-product can be separated by a conventional method such as extraction.

As described above, according to the process of the present invention, organic carbonates used as an intermediate material useful in chemical industry can be produced efficiently.

Consequently, the present invention is practically highly advantageous in the field of chemical industry, as a process for efficiently producing an organic carbonate which can be used as the starting material for intermediate materials of various chemical products including the intermediates for producing polycarbonate (such as aryl carbonate) and the intermediates of pharmaceuticals or agricultural chemicals (such as alkyl carbonate), or solvents.

The present invention will be described in greater detail with reference to examples and comparative examples as follows, provided that the present invention is not limited thereto.

EXAMPLE 1

In a 200 ml autoclave, 9.41 g (100 mmol) of phenol, 0.639 g (0.3 mmol) of palladium/active carbon (containing 5% by weight of palladium, produced by N. E. Chemcat Corporation), 0.164 g (0.9 mmol) of copper (II) acetate, 1.451 g (4.5 mmol) of tetra-N-butylammonium bromide, 0.496 g (4.5 mmol) of hydroquinone, and 50 ml of methylene chloride were sealed. The air in said autoclave was substituted by carbon monoxide by pressurizing and depressurizing with carbon monoxide. Then, the carbon monoxide was pressurized so that it is 60 kg/cm²G at 25° C., and further pressurized so that the concentration of oxygen is 5% by volume, and then heated to 100° C., and reacted for 3 hours. In the course of reaction, gas was analyzed every one hour, and pressure was applied so that the concentration of oxygen is 5% by volume. After being cooled and depressurized, and the gas and the reaction solution were analyzed by gas chromatography. As the result, 14.3 mmol of diphenyl carbonate was produced, and 0.2 mmol of phenylsalicylate and 51.3 mmol of carbon dioxide resulted as by-products.

EXAMPLE 2

The same reaction as in Example 1 was repeated except that 0.040 g (0.15 mmol) of $PdBr_2$ was used in place of palladium/active carbon. As the result of analyzing the gas and the reaction solution by gas chromatography, 11.9 mmol of diphenyl carbonate was produced, and 0.2 mmol of phenyl salicylate, and 47.8 mmol of carbon dioxide were produced as by-products.

COMPARATIVE EXAMPLE 1

The same reaction as in Example 1 was repeated except that 0.224 g (0.9 mmol) of tetrahydrate of cobalt acetate was used in place of copper(II) acetate. As the result of analyzing the gas and the reaction solution by gas chromatography, 7.6 mmol of diphenyl carbonate was produced, and 0.2 mmol of phenyl salicylate, and 53.5 mmol of carbondioxide were produced as by-products.

COMPARATIVE EXAMPLE 2

The same reaction as in Example 1 was repeated except that 0.317 g (0.9 mmol) of $Mn(acac)_3$ was used in place of copper(II) acetate. As the result of analyzing the gas and the reaction solution by gas chromatography, 6.9 mmol of diphenyl carbonate was produced. In addition, as by-products, 0.1 mmol of phenyl salicylate, and 43.3 mmol of carbon dioxide were produced. Therein, acac indicates acetyl acetonato.

COMPARATIVE EXAMPLE 3

The same reaction as in Comparative Example 1 was repeated except that hydroquinone was not used. As the result of an analysis of the gas and the reaction solution by gas chromatography, 0.4 mmol of diphenyl carbonate was produced. In addition, by-products, 11.0 mmol of carbon dioxide was produced. Production of phenyl salicylate was not confirmed.

COMPARATIVE EXAMPLE 4

The same reaction as in Comparative Example 1 was repeated except that 0.83 g (4.5 mmol) of tri-n-butylamine was used in place of tetra-N-butylammonium bromide. As the result of analyzing the gas and the reaction solution by gas chromatography, 0.3 mmol of diphenyl carbonate was produced, and as by-products, 6.4 mmol of carbon dioxide was produced. Production of phenyl salicylate was not confirmed there.

EXAMPLE 3

The same reaction as in Example 1 was repeated except that 0.040 g (0.15 mmol) of $PdBr_4$ and 1,4-dihydroxynaphthalene were used in place of palladium/active carbon and hydroquinone. As the result of analyzing the gas and the reaction solution by gas chromatography, 10.6 mmol of diphenyl carbonate was produced, and as by-products, 0.2 mmol of phenyl salicylate and 23.5 mmol of carbon dioxide were produced.

EXAMPLE 4

The same reaction as in Example 1 was repeated except that 11.41 g (50 mmol) of bisphenol A was used in place of phenol. After the reaction, methylene chloride was distilled away, and the concentrate was put into 720 ml of methanol, then a white crystal precipitated. The crystal was separated by filtration, washed several times with methanol and dried to obtain 0.844 g of a white powdery solid. As the result of analysis by the infrared absorption(IR) spectrum (KBr pellet method), and an analysis by ordinary temperature gel permeation chromatography (GPC) using tetrahydrofuran as solvent and polystyrene as the reference material, it was confirmed that the solid obtained was polycarbonate, from that IR absorption at 1769.0 $cm^{-1}$ derived from carbonyl group (—CO—) in the carbonate bond. The molecular weight of said solid (polymer) was 1153 in weight average molecular weight (Mw), and 922 in number average molecular weight (Mn), and Mw/Mn was 1.25. FD-MS (Field Disorption Mass Spectrometry) and $^1$H-NMR analysis showed that the product was about a trimer or tetramer, and a cyclic oligomer was produced as well as a straight chain oligomer (the ratio of straight chain/cyclic oligomer: about 15). The amount of carbon dioxide produced was 43.0 mmol.

EXAMPLE 5

The same reaction as in Example 1 was repeated except that p-t-butylphenol was used in place of phenol. As the result of analysis of the gas and the reaction solution by gas chromatography, 12.8 mmol of di(p-t-butylphenyl) carbonate was produced, and as by-products, 46.7 mmol of carbon dioxide was produced. Production of phenyl salicylate was not confirmed.

What is claimed is:

1. A process for producing an organic carbonate which comprises reacting (i) an aromatic hydroxy compound which is at least one compound selected from the group consisting of an aromatic monohydroxy compound and an aromatic polyhydroxy compound, (ii) carbon monoxide, and (iii) oxygen in the presence of a catalyst comprising (a) palladium or a palladium compound, (b) a cuprous compound or a cupric compound, (c) at least one compound selected from the group consisting of a quinone and an aromatic diol formed by reduction of the quinone, and (d) a halogenated onium compound.

2. The process according to claim 1, wherein the aromatic hydroxy compound is at least one compound selected from the group consisting of an aromatic monohydroxy compound having 6 to 15 carbon atoms, and an aromatic polyhydroxy compound having 6 to 15 carbon atoms.

3. A process according to claim 1, wherein the organic hydroxy compound is an aromatic monohydroxy compound having 6 to 15 carbon atoms or an aromatic polyhydroxy compound having 6 to 15 carbon atoms.

4. The process according to claim 1, wherein the aromatic hydroxy compound is an aromatic monohydroxy compound which is phenol, cresol, naphthol, p-methylphenol, or t-butylphenol.

5. The process according to claim 3, wherein the aromatic hydroxy compound is an aromatic polyhydroxy compound which is catechol, hydroquinone, resorcinol or bisphenol A.

6. The process according to claim 1, wherein (a) is a palladium compound which is palladium chloride, palladium bromide, palladium iodide, palladium acetate, palladium nitrate, or palladium sulfate.

7. The process according to claim 1, wherein (a) is a palladium which is deposited on active carbon, alumina, silica, silica.alumina, or zeolite.

8. The process according to claim 1, wherein (b) is a cuprous compound which is cuprous chloride, cuprous bromide, or cuprous iodide.

9. The process according to claim 1, wherein (b) is a cupric compound which is cupric chloride, cupric bromide, cupric iodide, cupric acetate, or cupric nitrate.

10. The process according to claim 1, wherein (c) is a quinone which is benzoquinone, 1,2-benzoquinone, 1,4-naphthoquinone, anthraquinone, or 1,4-phenanthrenequinone.

11. The process according to claim 1, wherein (c) is an aromatic diol which is hydroquinone, catechol, 1,4-dihydroxynaphthalene, 9,10-dihydroxyanthracene, or 1,4-dihydroxyphenanthrene.

12. The process according to claim 1, wherein the halogenated onium compound is tetraalkylammonium halide, tetraalkylphosphonium halide, or trialkylsulfonium halide.

13. The process according to claim 12, wherein the tetraalkylammonium halide is $(C_3H_7)_4NCl$, $(C_4H_9)_4NCl$ $(C_3H_7)_4NBr$, $(C_4H_9)_4NBr$, $(C_3H_7)_4NI$, or $(C_4H_9)_4NI$.

14. The process according to claim 12, wherein the tetraalkylphosphonium halide is $(C_3H_7)_4PCl$ $(C_4H_9)_4PCl$, $(C_3H_7)_4PBr$, $(C_4H_9)_4PBr$, $(C_3H_7)_4PI$, or $(C_4H_9)_4PI$.

15. The process according to claim 12, wherein the trialkylsulfonium halide is $(C_3H_7)_3SCl$, $(C_4H_9)_3SCl$, $(C_3H_7)_3SBr$, $(C_4H_9)_3SBr$ $(C_3H_7)_3SI$, or $(C_4H_9)_3SI$.

16. The process according to claim 1, wherein the reaction temperature is 50 to 200° C., the partial pressure of carbon monoxide is at least 30 kg/$cm^2$, and the partial pressure of oxygen is at least 1 kg/$cm^2$.

17. The process according to claim 15, wherein component (a) is in an amount of $10^{-5}$ to 1 mol as Pd based on 1 mol of the aromatic hydroxy compound; component (b) is in an amount of 1 to 100 moles, based on 1 mol of Pd as component (a); component (c) is in an amount of 1 to 100 mol, based on 1 mol of Pd as component (a) ; component (d) is in an amount of 1 to 100 mol, based on 1 mol of Pd as component (a); and the process is carried out at a temperature of 70° to 150° C.

18. The process according to claim 1, wherein component (a) is in an amount of $10^{-4}$ to $10^2$ mol as Pd based on 1 mol of the aromatic hydroxy compound; component (b) is in an amount of 1 to 50 moles, based on 1 mol of Pd as component (a); component (c) is in an amount of 1 to 50 mol, based on 1 mol of Pd as component (a); component (d) is in an amount of 1 to 50 mol, based on 1 mol of Pd as component (a); and the process is carried out at a temperature of 70° to 150° C.; the carbon monoxide is at a partial pressure of at least 30 kg/$cm^2$G; the partial pressure of oxygen is at least 1 kg/$cm^2$G; which further comprises carrying out the process in the presence of a solvent selected from the group consisting of hexane, heptane, cyclohexane, benzene, toluene, xylene, methylene chloride, chloroform, chlorobenzene, dioxane, anisole, diphenylether, methyl acetate, ethyl acetate, phenyl acetate, methyl propionate and ethyl pinonate.

19. The process according to claim 18, wherein the aromatic hydroxy compound is selected from the group consisting of phenol cresol, naphthol, p-methylphenol, t-methylphenol, catechol, hydroquinone, resorcinol and bisphenol A; component (a) is selected from the group consisting of palladium, palladium chloride, palladium bromide, palladium iodide, palladium acetate, palladium nitrate and palladium sulfate; component (b) is selected from the group consisting of cuprous chloride, cuprous bromide, cuprous iodide, cupric chloride, cupric bromide, cupric iodide, cupric acetate and cupric nitrate; component (c) is selected from the group consisting of benzoquinone, 1,2-benzoquinone, 1,4-naphthoquinone, anthraquinone, 1,4-phenanthrenequinone, hydroquinone, catechol, 1,4-dihydroxynaphtholene, 9,10-dihydroxyanthracene and 1,4-dihydroxyphananthrene; and compound (d) is selected from the group consisting of $(C_3H_7)_4NCl$, $(C_4H_9)_4NCl$, $(C_3H_7)_4NBr$, $(C_4H_9)_4NBr$, $(C_3H_7)_4NI$, $(C_4H_9)_4NI$, $(C_3H_7)_4PCl$, $(C_4H_9)_4PCl$, $(C_3H_7)_4PBr$, $(C_4H_9)_4PBr$, $(C_3H_7)_4PI$, $(C_4H_9)_4PI$, $(C_3H_7)_3SCl$ $(C_4H_9)_3SCl$, $(C_3H_7)_3SBr$, $(C_4H_9)_3SBr$, $(C_3H_7)_3SI$, or $(C_4H_9)_3SI$; and the partial pressure of carbon monoxide is 60 kg/cm$^2$G.

* * * * *

UNITED STATES PATENT AND TRADEMARK OFFICE
CERTIFICATE OF CORRECTION

PATENT NO. : 5,336,803
DATED : August 9, 1994
INVENTOR(S) : KEZUKA et al

It is certified that error appears in the above-identified patent and that said Letters Patent is hereby corrected as shown below:

Column 8, line 40, Claim 17:
        Delete "15" and insert --16--.

Signed and Sealed this

Twelfth Day of March, 1996

Attest:

BRUCE LEHMAN

*Attesting Officer*     Commissioner of Patents and Trademarks